United States Patent [19]

Elsheikh et al.

[11] Patent Number: 5,714,651
[45] Date of Patent: Feb. 3, 1998

[54] USE OF POLYMERIZATION INHIBITOR TO PROLONG THE LIFE OF A LEWIS ACID CATALYST

[75] Inventors: Maher Yousef Elsheikh, Wayne; Michael Sheppard Bolmer, Collegeville, both of Pa.

[73] Assignee: Elf Atochem North America, Inc., Philadelphia, Pa.

[21] Appl. No.: 579,818

[22] Filed: Dec. 28, 1995

[51] Int. Cl.$^6$ .............................. B01J 20/02; B01J 20/34; C07C 17/00; C07C 19/08
[52] U.S. Cl. ........................ 570/165; 570/166; 570/168; 502/33; 502/400; 502/418
[58] Field of Search ........................ 502/33, 400, 418; 568/716; 570/166, 168

[56] References Cited

U.S. PATENT DOCUMENTS

| 4,968,850 | 11/1990 | Franklin et al. | 570/166 |
| 5,336,816 | 8/1994 | Achord et al. | 510/168 |
| 5,449,842 | 9/1995 | Elsheikh | 570/765 |

Primary Examiner—S. Mark Clardy
Attorney, Agent, or Firm—Ratner & Prestia

[57] ABSTRACT

A method for extending the life of catalyst used to fluorinate olefins, e.g. a supported Lewis acid catalyst in the catalytic hydrofluorination of vinylidene chloride by conducting the hydrofluorination in the presence of a polymerization inhibitor for the vinylidene chloride.

11 Claims, 1 Drawing Sheet

USE OF POLYMERIZATION INHIBITOR TO PROLONG THE LIFE OF A LEWIS ACID CATALYST

FIELD OF THE INVENTION

This invention is directed to the catalytic fluorination of olefins. One aspect of the invention relates to the process wherein a Lewis acid catalyst (e.g. $SnF_4$ on activated carbon, hereinafter sometimes referred to as "Sn/C") is used in the gas or liquid phase catalytic hydrofluorination of vinylidene chloride (VDC) to 1,1-dichloro-1-fluoroethane (141$b$), 1-chloro-1,1-difluoroethane (142$b$), and 1,1,1-trifluoroethane (143$a$).

BACKGROUND OF THE INVENTION 1,1-dichloro-1-fluoroethane (141$b$) and 1-chloro-1,1-difluroethane (142$b$) are HCFCs with reduced ozone depletion potential (ODP) used to replace CFCs 11 and 12 for foam blowing, and to replace CFC 113 for solvent cleaning. Also it is known that 142$b$ can be dehydrochlorinated to 1,1 difluoroethylene (1132$a$). 143$a$ is an HFC with zero ODP used in refrigerant blends. These products are currently manufactured in the industry by hydrofluorination of methylchloroform using HF in the liquid phase, or by hydrofluorinating 1,1-dichloroethylene (1130$a$) in the liquid phase or gas phase.

U.S. Pat. No. 4,968,850 describes the use of triethyl phosphite $P(OC_2H_5)_3$, inhibitor to reduce the level of VDC polymerization by approximately 50%. This means that polymerization of VDC can take place, even when 0.05 mole of triethyl phosphite inhibitor (5 mole% of VDC used (50,000 ppm) or 100% from the $SnCl_4$ used), and hence a shorter catalyst life time is expected.

U.S. Pat. No. 5,336,816 claims a process to manufacture 141$b$ in the liquid phase, by adding HF to VDC using Ti (IV) salt in the presence of dimethylsulfone as a solvent. The amount of tar formed using this solvent was claimed to be less than 5%.

In U.S. Pat. No. 5,449,842, a gas phase process is described wherein the heterogeneous catalyst $SnF_4$/Carbon can be used efficiently to add HF in the gas phase to 1,1-dichloroethylene (VDC; "1130$a$") *to form the desirable product* 1,1-dichloro-1-fluoroethane (141$b$) and 1,1-difluoro-1-chloroethane (142$b$) selectively depending on the processing condition. While the VDC contains p.methoxyphenol, used by the manufacture as a storage inhibitor, the p.methoxyphenol was removed prior to hydrofluorination of the VDC.

When the process described above with reference to U.S. Pat. No. 5,449,842 ran continuously for an extended period of time (600 hours), we noticed that the catalyst activity was decreasing, i.e., there was more of 141$b$ formed at the expense of 142$b$ selectivity. This decrease in the catalyst activity was attributed to the formation of a thin film of polyvinylidene chloride (PVDC) on the catalyst.

Catalyst deactivation requires regular shut-down of the reactor for either regeneration or replacing the catalyst bed itself. This is an additional expense which makes such processes economically less attractive.

SUMMARY OF THE INVENTION

The present invention in its broadest aspects is a method for prolonging the useful life of a solid catalyst used in the fluorination of olefins. In particular the present invention pertains to an improved process for fluorinating olefins (e.g. VDC) in which the olefin (VDC) is fed to the reactor together with a small amount of a polymerization inhibitor, e.g. p.methoxyphenol. Despite the fact that the inhibitor is a solid and might be expected to be adsorbed by the catalyst support (activated carbon) and cover the active sites of the catalyst, it was found, unexpectedly, that the process could run continuously for at least 600 hours without any evidence of catalyst deactivation. A similar result was obtained when the process of the present invention was run in the liquid phase. After 250 hours of continuous running there was no evidence of catalyst deactivation, polymer formation or loss of tin.

In a preferred embodiment of the invention p.methoxyphenol is an inhibitor that when used at a very low level (e.g. 200 ppm by weight) will prevent polymerization of VDC from either the gas or liquid phase and enhance the life of the catalyst.

DETAILED DESCRIPTION OF THE INVENTION

Figure 1:
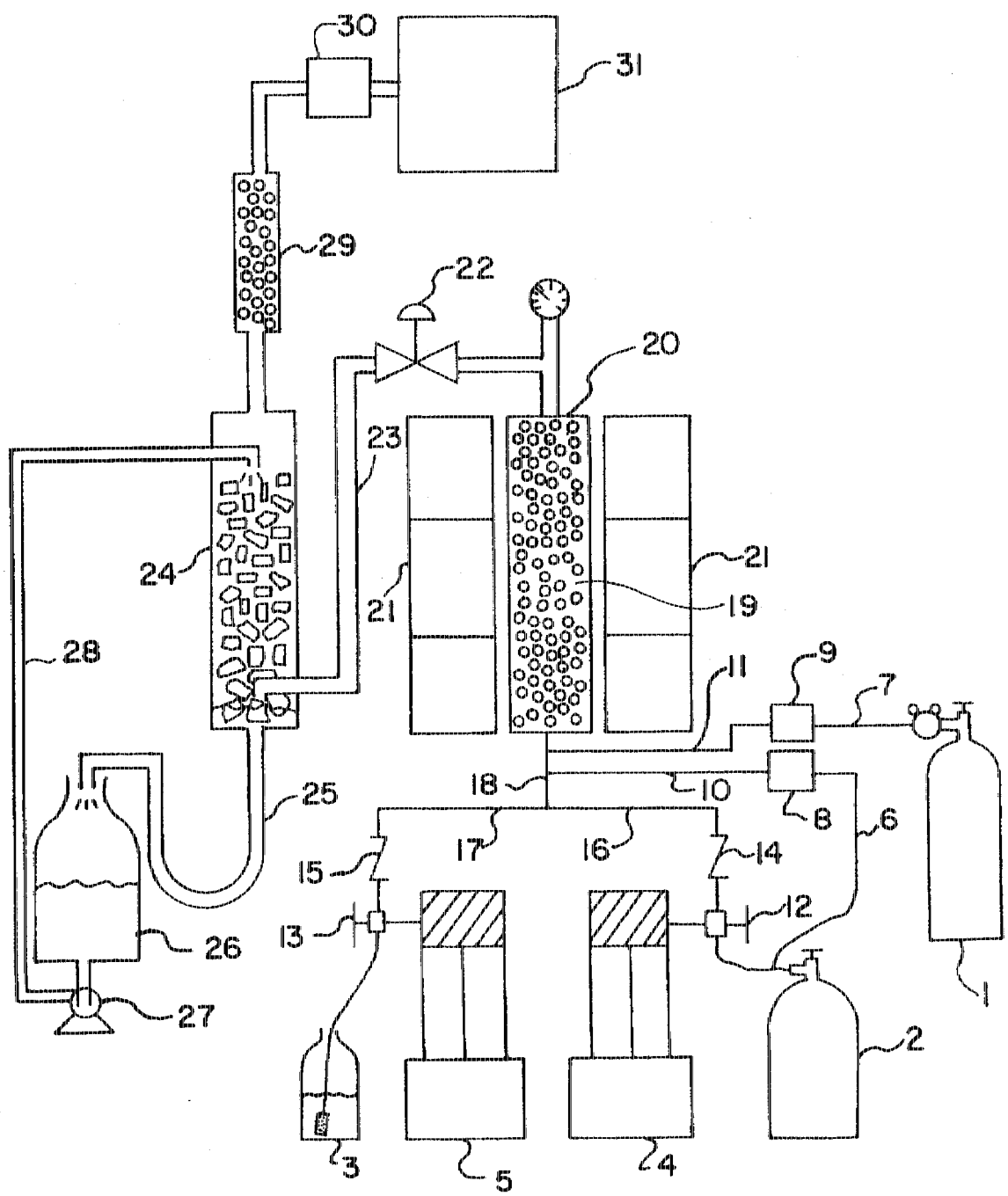
FIG. 1 is a schematic diagram of liquid phase process according to the invention.

In the processes of this invention (catalytic hydrofluorination of olefins using a supported catalyst), in addition to p. methoxyphenol, other polymerization inhibitors such as limonene, d,1-limonene, quinones, hydroquinones, epoxides and amines can be used. The level of the inhibitor used can vary between 10 and 500 ppm by weight.

The process can be run in the liquid phase as well as the gas phase, as either a batch or continuous process.

The operating temperature can be between 0° C. and 300° C., and is preferably between 30° and 150° C. for the gas phase, and between 0° and 100° C. for the liquid phase.

The pressure can be between 0 and 1000 psig. It is preferred to run the reaction at a pressure between 10 psi and 200 psig. The vapor pressures of the reactants and products should be considered when setting the temperature and pressure to give either a gas phase or liquid phase reaction.

Contact time (reactor volume/volumetric flow rate of feed calculated at operating temperature and pressure) can be varied between 1 and 200 seconds for the gas phase process and between 1 minute and 20 hours for the liquid phase process.

The molar ratio of HF to VDC can be between 0.1 and 10, and preferably is between 1 and 4.

The catalyst may comprise salts (preferably chlorides) of the following Lewis acid species: tin (IV), bismuth (III), antimony (V), and titanium (IV). The chlorides are converted to the corresponding fluorides upon activation with hydrogen fluoride.

The catalyst may be supported on an appropriate catalyst support, such as activated carbon, graphite, fluorided graphite or fluorinated aluminum oxide. Such supported catalysts may be employed, for example, in the form of pellets or granules. Tin (IV) salts, preferably $SnCl_4$, are particularly useful. Upon HF activation, the resulting solid $SnF_4$ catalyst remains strongly adhered to the carbon support.

The following examples are presented to illustrate the practice of the invention, but are not intended to limit the scope thereof. In these examples, the effectiveness of the presently preferred polymerization inhibitor for VDC, p.methoxyphenol, in extending the useful life of the catalyst Sn/C is demonstrated.

In the examples, the product stream was scrubbed and dried, then analyzed with a gas chromatograph. Optimum conditions were not employed in all the examples, which are intended primarily to illustrate the effects on the catalyst life of including a polymerization inhibitor for VDC in the VDC feed.

EXAMPLE 1

Performance of the Catalyst in Absence of Inhibitor

(Comparative Example)

The catalyst (containing 0.0017 mole $SnCl_4$/gram of the catalyst) was prepared as described in U.S. Pat. No. 5,449,842, the specification of which is incorporated herein by reference. In particular, the activated carbon-supported $SnCl_4$ was heated in a stream of nitrogen at 50° C. to purge the air out of the reactor, followed by feeding HF and nitrogen gases over the catalyst until it was fluorinated. The catalyst (100 grams) was loaded into a reactor which was directly connected to a gas chromatograph as described in the U.S. Patent referred to above. The catalyst was evaluated at 75° and 135° C.

At 75° C., HF gas was fed at a rate of 0.06 g/min. and the VDC liquid at a rate of 0.123 g/min.). The contact time was 88 seconds. Gas chromatography analysis of the product obtained, expressed in mole %, showed 100% conversion. The selectivity for 141b was 32.5%; for 142b, 62.8%; and for 143a, 4.6%. After running for 36 hours, conversion was still 100%. However, the selectivity for 141b increased to 52.3%, while that for 142b and 143a decreased to 44.1% and 3.6%, respectively.

At 135° C., using a contact time of 77 seconds and using the same feed conditions for HF and VDC, conversion was 100%, selectivity for 141b was 19.8%; for 142b, 65.1%, and for 143a, 15.1%. After running for 132 hours, selectivity for 141b increased to 58.87%, while selectivity for 142b and 143a decreased to 36.4% and 4.7%, respectively. Despite the fact that we were able to maintain high conversion all the time, selectivity for the higher fluorination products, namely 142b and 143a was decreasing. Meanwhile, the selectivity for the lower fluorination product (141b) was increasing. This is considered to be a result of deactivation of the catalyst.

EXAMPLE 2

Performance of the Catalyst Sn/C When 200 ppm of p.methoxyphenol is Included in the VDC Feed (Gas Phase)

VDC (0.1 g/m containing 200 ppm of p.methoxyphenol) as a liquid was fed directly to the catalyst bed (97 grams) together with HF (0.067 g/min.) at 150° C. The contact time was 42.5 seconds at atmospheric pressure. This produced 100% conversion, with selectivity of 65%; for 142b, 25% for 141a, and 10% for 143a. After 600 hours of continuous run, conversion was still 100%, and the selectivity for 141b, 142b and 143a was nearly constant at 25%, 65% and 10%, respectively.

EXAMPLE 3

Liquid Phase Performance of Sn/C Catalyst When 200 ppm of p.methoxyphenol is Included in the (Liquid) VDC Feed As described in detail below, hydrofluorination of VDC in the liquid phase produced no evidence of VDC polymer formation or loss of catalyst activity.

A diagram of the process is shown in FIG. 1. In order to perform the process, 78 grams of catalyst 19 were loaded into the reactor 20, made of a Hastelloy-C tube (11 inches long and ¾ inch in diameter). The reactor 20 was heated to 50° C. in a 3-zone furnace 21. HF from cylinder 2 and dry nitrogen from cylinder 1 were passed via conduits 6 and 7 through flow controllers 8 and 9 respectively and via conduits 10 and 11 respectively into reactor 20 and over the catalyst 19 in a volume ratio of 2:1 for 18 hours to convert the catalyst 19 from $SnCl_4$ to $SnF_4$, producing HCl byproduct. The exit gases from reactor 20 passed through a back-pressure regulator 22, which was open to operate at atmospheric pressure, then via conduit 23 to a scrubber 24. Unreacted HF and byproduct HCl were absorbed in scrubber 24 with KOH solution circulating from tank 26 through conduits 25 and 28 using pump 27.

Next, syringe pumps 4 and 5 were filled with liquid HF from cylinder 2 and liquid VDC (containing 200 ppm of p-methoxyphenol) from container 3 through three-way valves 12 and 13. After pumps 4 and 5 were filled, the three-way valves 12 and 13 were positioned to introduce HF and VDC containing p-methoxyphenol into reactor 20 through check valves 14 and 15 and conduits 16, 17 and 18. First, the reactor 20 was filled with liquid HF using pump 4, with backpressure valve 22 set at 100 psi; then the VDC pump 5 was also started. Product gas passed from the caustic scrubber 24 to a packed bed of anhydrous calcium sulfate 29 to remove water, and then to a sample valve 30 that injected gas samples into a gas chromatograph 31.

A range of test conditions and the corresponding results are summarized in Table 1.

TABLE 1

LIQUID-PHASE REACTION OF VDC AND HF

| Temp °C. | Press (psig) | Time (hr.) | HF/VCl$_2$ | Conv. % | 143a % | 142b % | 141b % | 140a % |
|---|---|---|---|---|---|---|---|---|
| 50 | 57 | 18.1 | 1.1 | 96.9 | 0.1 | 0.6 | 99.3 | 0.0 |
| 50 | 87 | 15.2 | 2.0 | 98.3 | 0.0 | 0.2 | 99.7 | 0.1 |
| 60 | 73 | 9.1 | 1.1 | 100.0 | 0.2 | 0.6 | 99.1 | 0.1 |
| 60 | 101 | 3.6 | 1.1 | 100.0 | 0.1 | 0.1 | 99.5 | 0.3 |
| 75 | 74 | 9.4 | 1.1 | 100.0 | 0.5 | 21.9 | 77.5 | 0.1 |

At a pressure of 57 psig, a temperature of 50° C., feed rates of 0.083 g/min. of VDC and 0.019 g/min. of HF, for a molar feed ratio of 1.1:1 HF:VDC, conversion of VDC was 97%, with selectivity of 99.3% 141b, 0.6% 142b, 0.1% 143a.

At a pressure of 101 psig, a temperature of 60° C., feed rates of 0.42 g/min. VDC and 0.095 g/min. HF for a molar feed ratio of 1.1:1 HF:VDC, conversion of VDC was 100%, and selectivity for 141b was 99.5%. The catalyst was used for over 250 hours of continuous reaction. At the end of the reaction, there were no visible signs of polymer formation, and conversion had increased to 100%.

The pressure in the reactor 20 was such that HF, VDC, and 141b were in the liquid phase, but HCl, 142b, and 143a could vaporize.

The process of the present invention is useful to produce raw material to convert to vinylidene fluoride or to separate the raw material into commercially useful components.

While the invention has been described herein with reference to specific embodiments, it is not limited thereto. Rather it should be recognized that this invention may be practiced as outlined above within the spirit and scope of the appended claims, with such variants and modifications or may be made by those skilled in this art.

What is claimed:

1. A process for prolonging the life of a solid supported catalyst used to fluorinate olefin comprising the step of conducting said fluorination in the presence of a polymerization inhibitor for said olefin.

2. A process for converting vinylidene chloride to 141$b$ plus 142$b$ plus 143$a$ in the presence of a solid supported catalyst without premature failure of the catalyst comprising the step of conducting said reaction in the presence of a polymerization inhibitor for said vinylidene chloride.

3. In a process for producing vinylidene fluoride by the reaction of hydrogen fluoride and vinylidene chloride in the presence of a solid supported Lewis acid catalyst, the improvement which comprises conducting said reaction in the presence of a polymerization inhibitor for said vinylidene chloride.

4. A process as in claim 3 wherein said catalyst comprises a compound selected from the group consisting of $BiF_3$, $SbF_5$, $SnF_4$, and $TiF_4$ supported on activated carbon.

5. A process as in claim 3 wherein said polymerization inhibitor is p.methoxyphenol.

6. A process as in claim 3 wherein said polymerization inhibitor is admixed with said vinylidene chloride before said reaction is initiated.

7. A process as in claim 6 wherein said polymerization inhibitor is present in amount equal to from about 10 to about 500 ppm based on the amount of the vinylidene chloride feed.

8. A process as in claim 2 wherein said polymerization inhibitor is admixed with said vinylidene chloride before said reaction is initiated.

9. A process as in claim 2 wherein said polymerization inhibitor is present in amount equal to from about 10 to about 500 ppm based on the amount of the vinylidene chloride feed.

10. A process as in claim 9 wherein said amount of inhibitor is 200 ppm.

11. In a process for producing vinylidene fluoride by the reaction of hydrogen fluoride and vinylidene chloride in the presence of a supported Lewis acid catalyst, the improvement which comprises conducting said reaction in the presence of p.methoxyphenol as a polymerization inhibitor for said vinylidene chloride.

* * * * *